United States Patent

Schulz et al.

[11] Patent Number: 4,744,811
[45] Date of Patent: May 17, 1988

[54] SUBSTITUTED OXIME-ETHERS AND THEIR USE AS BIOREGULATORS TO LOWER THE ENDOGENOUS ETHYLENE LEVEL IN PLANTS

[75] Inventors: Guenter Schulz, Ludwigshafen; Wolfgang Will, Kirchheim; Johann Jung; Hansjoerg Fritsch, both of Limburgerhof, all of Fed. Rep. of Germany

[73] Assignee: BASF Aktiengesellschaft, Ludwigshafen, Fed. Rep. of Germany

[21] Appl. No.: 35,730

[22] Filed: Apr. 8, 1987

[30] Foreign Application Priority Data

Apr. 23, 1986 [DE] Fed. Rep. of Germany ....... 3613649

[51] Int. Cl.$^4$ .................. A01N 3/02; A01N 37/00; C07C 69/74; C07C 101/02
[52] U.S. Cl. .................................. 71/68; 71/106; 560/121; 560/125; 560/168
[58] Field of Search .................. 560/125, 121, 168; 71/106, 68

[56] References Cited

U.S. PATENT DOCUMENTS 4,584,014  4/1986  Patterson .................. 560/125 X

FOREIGN PATENT DOCUMENTS 1443555  7/1976  United Kingdom .................. 71/106

Primary Examiner—Michael L. Shippen
Assistant Examiner—Patricia M. Scott
Attorney, Agent, or Firm—Keil & Weinkauf

[57] ABSTRACT

Substituted oxime-ethers of the formulae

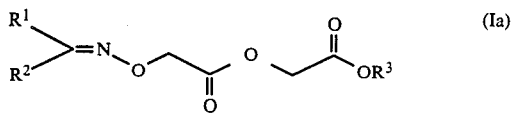

(Ia)

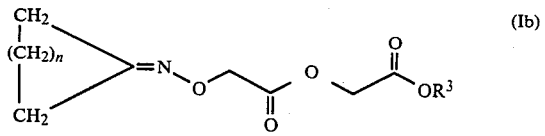

(Ib)

where $R^1$ and $R^2$ independently of one another are $C_1$-$C_6$-alkyl, n is 2 or 3 and $R^3$ is hydrogen or $C_1$-$C_6$-alkyl.

3 Claims, No Drawings

SUBSTITUTED OXIME-ETHERS AND THEIR USE AS BIOREGULATORS TO LOWER THE ENDOGENOUS ETHYLENE LEVEL IN PLANTS

The present invention relates to novel substituted oxime-ethers and to their use as bioregulators, especially for lowering the endogenous ethylene level in plants.

Ethylene, formed naturally in green plants or acting from outside, acts as a plant hormone which controls senescene (aging) phenomena in plants. Lowering the endogenous ethylene level as a rule delays senescence. This effect can be utilized in various ways: as Examples, there may be mentioned lengthening the life of cut flowers, reducing fruit abscission and lengthening the reproductive phase of plants to increase the yield on harvesting.

Hitherto, success in lowering the endogenous ethylene level has virtually been confined to the experimental scale; there are various obstacles in the way of industrial application, for example expensive manufacture and toxicity to humans in the case of aminoethoxyvinylglycine, phytotoxicity and nonspecific action in the case of aminooxyacetic acid or environmental pollution in the case of $Co^{++}$ ions. A comprehensive review is given in Ann. Rev. Plant Physiol. 1984, pages 155–189.

We have now found that active substances which may be described as substituted oxime-ethers and which have the general formula Ia or Ib

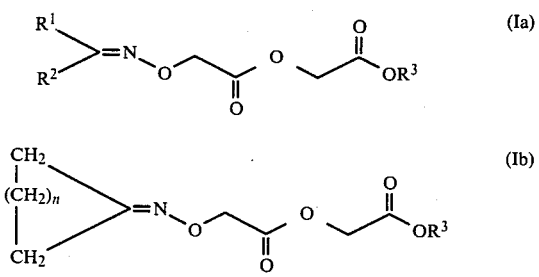

where $R^1$ and $R^2$ independently of one another are $C_1$–$C_6$-alkyl, n is 2 or 3 and $R^3$ is hydrogen or $C_1$–$C_6$-alkyl, have a bioregulating action in the above sense, in addition are distinguished by good plant toleration, and can be prepared in a simple manner. Furthermore, the active substances according to the invention are frequently water-soluble or at least, in many cases, readily soluble, so that their formulation is easy. Information on formulation may for example be found in the book by R. Cremlyn, Pesticides (1987), pages 14–18.

The following is one of several possible processes of preparation:

The starting material is a corresponding carboxylic acid of the formula IIa or IIb

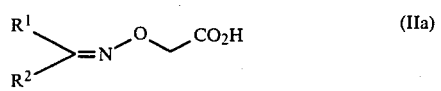

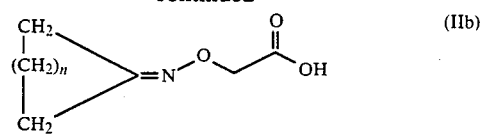

which is esterified with a corresponding carboxylic acid derivative of the formula III

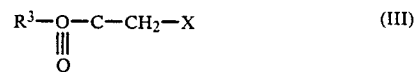

where X acts as a suitable reactive radical such as $I^-$, $Br^-$, $Cl^-$, or mesylate or tosylate. For economic reasons, the reactive radical (leaving group) generally used is chloride or bromide. Ester formation is carried out in a conventional manner in the presence of an acid acceptor such as an alkali metal or alkaline earth metal carbonate, especially sodium carbonate, or an alkali metal or alkaline earth metal hydroxide, especially sodium hydroxide, or an amine base, such as triethylamine, in the absence of a solvent or in an aprotic dipolar solvent such as dimethylformamide or N-methylpyrrolidone. The required intermediates II and III are in most cases commercially available materials, but in any case have been described and can at least be readily obtained by a man skilled in the art, using conventional means.

Depending on the nature of the substituents $R^1$ and $R^2$ the intermediates of the formula II and/or the active substances according to the invention may be in the form of E/Z isomers, which in general have different activity, or different intensity of activity.

$R^1$ and $R^2$ can be identical or different substituents and, if they are alkyl, can be n-alkyl or branched alkyl; $R^1$ and $R^2$ can, as shown, conjointly represent a methylene chain having 4 or 5 members; in that case, the formula Ib, shown separately for clarity, results.

$R^3$ can also be alkyl as well as benzyl, and in the latter case the benzyl may be substituted, for example by halogen, haloalkyl (especially trifluoromethyl), nitro, cyano or methyl. For economic reasons, in general up to three substituents may usefully be employed to achieve an acceptable improvement in action.

The general formulae I and Ia will also suggest, to a man skilled in the art, other processes of preparation, which may be selected in accordance with the available intermediates and which, in general, give comparable results. This emerges readily from the following equations:

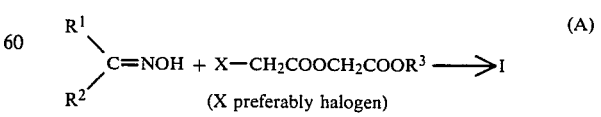

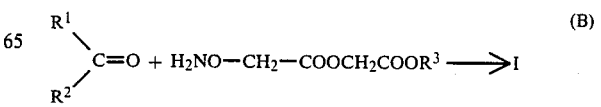

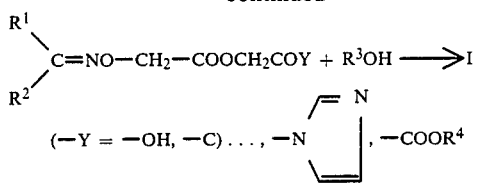

(—Y = —OH, —C)..., —N⟨N⟩, —COOR⁴ (D)

organic phase is washed with 1N HCl, aqueous NaHCO₃ solution and water and dried over Na₂SO₄. Distillation gives 152 g of compound 1, boiling point=75°-80° C. 0.2 mbar. ¹H-NMR (DCCl₃, in ppm); 1.85 s 3H, 1.90 s 3H, 3.75 s 3H, 4.70 s 4H.

The table which follows contains further compounds prepared in the same manner; where no physical data are shown, it is to be assumed that those compounds can be obtained in the same manner and/or exhibit the same type of action.

TABLE I

| Example No. | R¹ | R² | R³ | Melting point, °C. | Characteristic spectroscopic data ¹H-NMR (ppm) or IR |
|---|---|---|---|---|---|
| 2 | —CH₃ | —CH₃ | —C₂H₅ | | |
| 3 | —CH₃ | —CH₃ | —C₃H₇ | | |
| 4 | —CH₃ | —CH₃ | —CH(CH₃)₂ | Oil | 1.3 d 6H, 1.88 s 3H, 1.95 s 3H, 4.70 s 2H, 4.75 s 2H, 5.15 h 1H |
| 5 | —CH₃ | —CH₃ | —C(CH₃)₃ | Oil | 1.49 s 9H, 1.86 s 3H, 1.92 s 3H, 4.58 s 2H, 4.68 s 2H |
| 6 | —CH₃ | —CH₃ | —(CH₂)₅CH₃ | Oil | 0.90 t 3H, 1.30 m 6H, 1.65 m 2H. 1.88 s 3H, 1.92 s 3H, 4.18 t 2H, 4.70 s 4H |
| 7 | —CH₃ | —C₂H₅ | —CH₃ | | |
| 8 | —CH₃ | —C₂H₅ | —C₂H₅ | | |
| 9 | —CH₃ | —C₂H₅ | —C₃H₇ | | |
| 10 | —CH₃ | —C₂H₅ | —CH(CH₃)₂ | Oil | 1.05 t 3H, 1.25 d 6H, 1.90 s 3H, 2.18 q 2H, 4.62 s 2H, 4.70 s 2H, 5.10 h 1H |
| 11 | —CH₃ | —C₂H₅ | —C(CH₃)₃ | Oil | 1.05 t 3H, 1.50 s 9H, 1.92 s 3H, 2.18 q 2H, 4.58 s 2H, 4.70 s 2H |
| 12 | —CH₃ | —C₂H₅ | —(CH₂)₅CH₃ | Oil | 0.9 t 3H, 1.1 t 3H, 1.3 m 6H, 1.65 m 2H, 1.93 s 3H, 2,2 q 2H, 4.18 t 2H, 4.68 s 2H, 4.70 s 2H |
| 13 | | —(CH₂)₅— | —CH₃ | | |
| 14 | | —(CH₂)₅— | —C₂H₅ | | |
| 15 | | —(CH)₅— | —C₃H₇ | | |
| 16 | | —(CH₂)₅— | —CH(CH₃)₂ | | 1.30 d 6H, 1.65 m 6H, 2.2 m 2H, 2.55 m 2H, 4.65 s 2H, 4.70 s 2H, 5.1 h 1H |
| 17 | | —(CH₂)₅— | —C(CH₃)₃ | | 0.95 t 3H, (1,3 m + 1.6 m) 14 H, 2.2 m 2H, 2.5 m 2H, 4.2 t 2H, 4.7 s 4H |
| 18 | | —(CH₂)₅— | —(CH₂)₅CH₃ | | 1.5 s 9H, 1.6 m 6H, 2.2 m 2H, 2.55 m 2H, 4.6 s 2H, 4.7 s 2H |

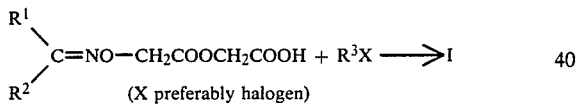

(X preferably halogen)

As will be seen, the possible molecular building blocks permit a plurality of types of reaction.

The preparation of the active substances according to the invention emerges especially from the following example:

Example 1

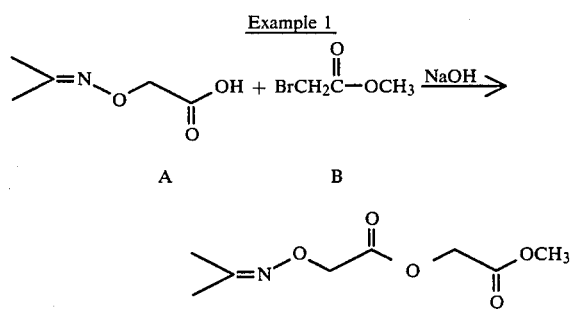

131 g of carboxylic acid A and 140 ml of triethylamine in 500 ml of DMF were stirred for 30 minutes at 20° C. 153 g of methyl bromoacetate (B) are slowly added dropwise and the batch is stirred for about 4 hours at 20° C. and 4 hours at 80° C. DMF is removed under reduced pressure (water pump); the residue is partitioned between methylene chloride and water and the

USE EXAMPLES

1. Inhibition of ethylene synthesis in pieces of soybean leaf

Pieces of soybean leaf were incubated with the active substances according to the claim, for 18 hours, then transferred into a vessel which can be closed gas-tight with a rubber septum, and incubated for a further 4 hours. The amount of ethylene formed was determined by gas chromatography. The inhibiting action of some typical examples is shown in Table II.

TABLE II

| Active substance | % Inhibition |
|---|---|
| H₂O | 0 |
| Amino-oxyacetic acid | 85 |
| 1 | 85 |
| 5 | 91 |
| 16 | 89 |
| 17 | 93 |

2. Wilting test on cut flowers (carnations)

Full-blown carnations were cut and were stood in a solution of the active substance. The course of wilting was observed over two weeks. Table III shows the percentage of flowers which still appeared fresh after 12 days.

TABLE III

| Active substance | % of flowers still fresh after 12 days |
|---|---|
| H₂O | 0 |
| Ag⁺ | 100 |
| 1 | 100 |

As the Examples show, the active substances according to the claim are able greatly to repress ethylene production in the tissues and to inhibit certain ethylene-dependent processes in the plants, for example wilting of flowers. The active substances employed are more easily accessible and/or less toxic than the known standard materials, namely amino-oxyacetic acid and silver salts.

USE EXAMPLES

1. Inhibition of ethylene synthesis in pieces of soybean leaf

Pieces of the leaves of 4–5-week-old soybean plants were preincubated with the active substances dissolved in water, acetone or a mixture of cyclohexanone and conventional emulsifiers, for example castor oil ethoxylate or calcium dodecylbenzenesulfonate, in a final concentration of 1 mM in 1 ml, for 8 hours; they were then transferred into a test tube and the latter was closed gas-tight with a rubber septum. After 4 hours, the amount of ethylene formed was determined by gas chromatography. The inhibiting action of some typical examples is shown in Table I. In the Table, 0 means 0–50% inhibition, (+) means 51–75% inhibition, (++) means 76–85% inhibition and (+++) means 86–100% inhibition.

TABLE I

| Active substance | Rating | Plant toleration* |
|---|---|---|
| Water | 0 | + |
| Amino-oxyacetic acid | ++ | − |
| 1 | +++ | + |
| 4 | ++ | + |
| 5 | +++ | + |
| 6 | +++ | + |
| 10 | ++ | + |
| 11 | +++ | + |
| 12 | + | + |
| 16 | +++ | + |
| 17 | +++ | + |
| 18 | ++ | + |

*The plant toleration was determined by spraying 6-week-old soybean plants with a solution of the active substance (3 mg/3 plants); + means good toleration and − means poor toleration.

2. Wilting test on cut flowers (carnations)

Full-blown carnations were but and stood in 100 ml of active substance solution. The active substances were dissolved in water, acetone or a mixture of cyclohexanone and conventional emulsifiers such as castor oil ethoxylate or calcium dodecylbenzenesulfonate. An assessment of wilting was made on the day on which all flowers in the water control had wilted: (0) means 0–25% fresh flowers, (+) means 26–50% fresh flowers, (++) means 51–85% fresh flowers and (+++) means 86–100% fresh flowers. The results are shown in Table II.

TABLE II

| Active substance | Concentration (mM) | Rating |
|---|---|---|
| Water | — | 0 |
| Amino-oxyacetic acid | 0.5 | + |
| 1 | 0.5 | +++ |
| 16 | 0.3 | ++ |
| 17 | 0.3 | +++ |

As the examples show, the active substances according to the claim are able greatly to repress ethylene production in the tissues and to inhibit certain ethylene-dependent processes in the plants, for example wilting of flowers. The active substances employed are more easily accessible, more effective and/or less toxic than the known standard materials, for example amino-oxyacetic acid or the silver salts also used.

We claim:

1. A substituted oxime-ether of the formula

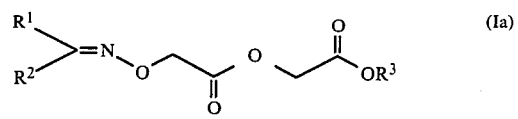

or

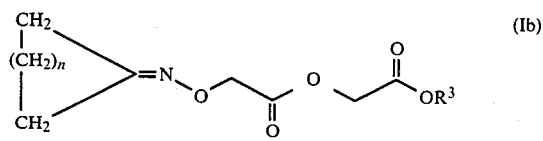

where $R^1$ and $R^2$ independently of one another are $C_1$–$C_6$-alkyl, n is 2 or 3 and $R^3$ is hydrogen or $C_1$–$C_6$-alkyl.

2. A composition for lowering the endogenous ethylene level in plants, which contains an effective amount of one or more compounds of the formula Ia or Ib as claimed in claim 1 with a solid or liquid carrier, with or without one or more surfactants.

3. A method of lowering the endogenous ethylene level in a plant comprising contacting a plant with an effective amount of one or more compounds as claimed in claim 1 or a composition as claimed in claim 2.

* * * * *